United States Patent [19]

McMahon et al.

[11] Patent Number: 5,332,838
[45] Date of Patent: Jul. 26, 1994

[54] CYCLIZATION PROCESS UTILIZING COPPER ALUMINUM BORATE AS A CATALYST

[75] Inventors: Patrick E. McMahon; Larry C. Satek, both of Wheaton, Ill.

[73] Assignee: Amoco Corporation, Chicago, Ill.

[21] Appl. No.: 174,822

[22] Filed: Mar. 29, 1988

[51] Int. Cl.$^5$ .................................. C07D 209/04
[52] U.S. Cl. .................................. 548/508
[58] Field of Search ........................ 548/508

[56] References Cited

U.S. PATENT DOCUMENTS

| | | | |
|---|---|---|---|
| 3,285,932 | 11/1966 | Illingworth | 548/508 |
| 3,699,120 | 10/1972 | Bakke | 548/508 |
| 4,024,171 | 5/1977 | McArthur | 518/715 |
| 4,590,324 | 5/1986 | Satek | 585/444 |
| 4,740,647 | 4/1988 | Hussmann | 585/411 |

*Primary Examiner*—Frederick E. Waddell
*Assistant Examiner*—William Jarvis
*Attorney, Agent, or Firm*—Thomas E. Nemo; Wallace L. Oliver; Frank J. Sroka

[57] ABSTRACT

The present invention is a cyclization process utilizing the catalyst copper aluminum borate which process comprises the step of contacting (1) a compound having a fragment in which a carbon-containing chain of at least three atoms in sequence is bonded at one end thereof to a nitrogen, oxygen, or sulfur atom, and at the opposite end to a carbon, nitrogen, oxygen, or sulfur atom, where the latter are bonded to at least one hydrogen atom; with (2) a catalyst comprising at least one member selected from the group consisting of copper aluminum borate and zero valent copper on a support comprising aluminum borate, under conditions sufficient to effect ring closure between the ends of the fragment to obtain a compound comprising a heterocyclic ring.

32 Claims, No Drawings

CYCLIZATION PROCESS UTILIZING COPPER ALUMINUM BORATE AS A CATALYST

FIELD OF THE INVENTION

The present invention relates generally to the use of copper aluminum borate as a cyclization catalyst. More particularly, the invention is directed to a cyclization process comprising the step of contacting (1) a compound having a fragment in which a carbon-containing chain of at least three atoms in sequence is bonded at one end thereof to a nitrogen, oxygen or sulfur atom, and at the opposite end to carbon, nitrogen, oxygen or sulfur, where the latter are bonded to at least one hydrogen atom, with (2) a catalyst comprising at least one member selected from the group consisting of copper aluminum borate or zero valent copper on a support comprising aluminum borate under conditions sufficient to effect ring closure between the ends of the fragment, thereby forming a heterocyclic ring. The cyclization process of the present invention can be used to manufacture a variety of useful compounds. For example, o-ethylaniline, o-ethylphenol, and o-ethylthiophenol can be cyclized to indole, benzofuran and benzothiofuran.

BACKGROUND AND PRIOR ART DISCUSSION

Indole (2,3-benzopyrole; FIG. 1 below) is a naturally occurring compound in plants and microorganisms. The indole ring system is found primarily in the amino acid tryptophan (2-amino-3-(3'-indolyl)-proprionic acid; FIG. 2 below), in plant hormones such as heterauxin (indole-3-acetic acid), in condensed ring alkyloids derived from tryptamine (2-(3'-indolyl)-ethylamine), and in complex monoterpene derived alkyloids such as strychnine and resetpine.

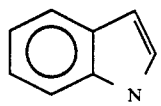

FIG. 1

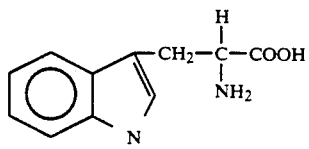

FIG. 2

The present market for indole is estimated to be approximately ½ million pounds. Indole derivatives are used primarily as fragrance enhancers and as intermediates in the manufacture of pharmaceuticals and dyes. Substantial growth in the market for indole would occur if there were demand for the compound as a starting material for industrially produced L-tryptophan, the latter being an essential amino acid useful as a dietary supplement for livestock feeds. However, at an estimated volume of 370,000 pounds, tryptophan is now used only in specialty applications. Its high cost will not support penetration into the potentially large tryptophan formulated feed markets.

Although tryptophan cannot be economically extracted from plant sources, it can be biosynthesized at relatively low cost by enzymatic condensation of L-serine and indole catalyzed by tryptophan synthetase in a free cell fermenter. Unfortunately, in the absence of any commercial process for manufacturing indole, supplies of indole for use in this synthesis must be obtained exclusively and at rather high cost from the 240°–260° C. fraction of coal tar distillate. The present price of indole therefore prevents biosynthesized tryptophan to make a substantial penetration into the formula feed market. Thus, need presently exists for an inexpensive commercial synthesis for indole which will open up the market for the use of tryptophan as an affordable dietary supplement in animal feeds.

Another potential route to the compound indole involves dehydrocyclization of o-ethylaniline. Unfortunately, commercial iron oxide and platinum on alumina catalysts elicit short lifetimes and poor regenerability when used for this reaction. Dehydrocyclizations of o-ethylaniline over iron oxide fall below 40 percent conversion after only 50 hours. Although platinum on alumina initially gives high conversion and selectivity, for this reaction conversion and selectivity decreased rapidly with time on stream. For example, conversion using a platinum on alumina catalyst decreased from 100 percent at 20 hours to 59 percent at 50 hours with a corresponding decrease in selectivity from 91 percent to 74 percent. Also, the platinum on alumina catalyst had poor regenerability with a sharp decline in activity and longevity after the first two regenerations. It is thus particularly desired to obtain a cyclization catalyst capable of converting o-ethylaniline to indole where such catalyst has an extended lifetime, high conversion and selectivity, and excellent regenerability when compared to commercial iron oxide or platinum on alumina catalysts which are inadequate for dehydrocyclization of o-ethylaniline.

The compound benzofuran, like indole, is also subject to limited availability and high price due to the lack of a commercial synthesis for the material. Presently, benzofuran is available only as a product of coal tar extract. This fact limits its use and discourages research into wider applications. Benzofuran, and benzofuran derivatives, have applications in coumarin-indene resins for floor tile, synthetic rubbers, and as bonding agents for composites.

SUMMARY OF THE INVENTION

The present invention is a cyclization process utilizing the catalyst copper aluminum borate which process comprises the step of contacting (1) a compound having a fragment in which a carbon-containing chain of at least three atoms in sequence is bonded at one end thereof to a nitrogen, oxygen, or sulfur atom, and at the opposite end to a carbon, nitrogen, oxygen, or sulfur atom, where the latter are bonded to at least one hydrogen atom; with (2) a catalyst comprising at least one member selected from the group consisting of copper aluminum borate and zero valent copper on a support comprising aluminum borate, under conditions sufficient to effect ring closure between the ends of the fragment to obtain a compound comprising a heterocyclic ring.

The invention is also directed to a cyclization process utilizing copper aluminum borate catalyst which process comprises the step of contacting (1) a starting compound comprising at least one five- or six-membered ring having ring substituents comprising (a) a first substituent selected from (i) a methyl group and (ii) a hydrocarbyl-containing group comprising a continuous sequence of two or more atoms, said sequence having a first atom selected from carbon, nitrogen, oxygen and sulfur bonded directly to the ring, and a second atom selected from carbon, nitrogen, oxygen and sulfur, having at least one hydrogen atom bonded thereto and separated by not more than one sequence atom from said first atom; and (b) a second substituent ortho to the first and comprising nitrogen, oxygen, or sulfur bonded directly to the ring or separated therefrom by a continuous sequence of not more than two atoms; with (2) a catalyst comprising at least one member selected from the group consisting of copper aluminum borate and zero valent copper on a support comprising aluminum borate under conditions sufficient to effect ring closure between said first and second substituents resulting in formation of a heterocyclic ring fused to the ring of the starting compound.

The present invention is further directed to a cyclization process utilizing the catalyst copper aluminum borate which comprises the step of contacting ( 1 ) a starting compound having a fragment characterized by the general formula A or B below:

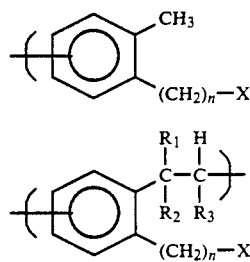

wherein $R_1$, $R_2$ and $R_3$, the same or different, are H or $C_1$ to $C_8$ hydrocarbyl and where $R_2$ and $R_3$ can be separate substituents or joined such that $R_2$, $R_3$, $C_1$ and $C_2$ constitute a ring; X is —NRR, —OR or —SR, such that the R groups, the same or different, are H or $C_1$ to $C_8$ hydrocarbyl; and n is an integer from 0 to 2; with (2) a catalyst comprising at least one member selected from the group consisting of copper aluminum borate and zero valent copper on a support comprising aluminum borate, under conditions sufficient to effect ring closure between the first and second ring substituents resulting in formation of a heterocyclic ring fused to the ring of the starting compound.

The present invention is further directed to a cyclization process utilizing the catalyst copper aluminum borate which comprises the step of contacting (1) a starting compound having the general formula below:

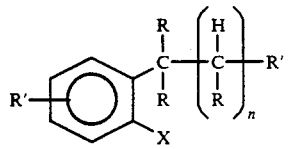

wherein X is —$NH_2$, —OH or —SH; wherein the R groups, being the same or different, are H or $C_1$ to $C_4$ hydrocarbyl; and the R' groups, being the same or different, are H or substantially hydrocarbyl; and n is 1 or 2; with (2) a catalyst comprising at least one member selected from the group consisting of copper aluminum borate or zero valent copper on a support comprising aluminum borate, under conditions sufficient to effect ring closure resulting in the formation of a heterocyclic fused ring compound.

The present invention provides a clean, inexpensive synthesis for indole from o-ethylaniline with high single pass conversions and very high selectivities. The copper aluminum borate catalyst has long term stability in this reaction showing no deactivation after over 200 hours on stream.

DETAILED DESCRIPTION

Copper aluminum borate and finely divided metallic copper on a support comprising aluminum borate are the subject of commonly assigned Zletz U.S. Pat. No. 4,729,979; of Zletz et al. U.S. Pat. No. 4,645,753 and of Satek U.S. Pat. No. 4,590,324. These patents disclose the preparation, characterization and utility of copper aluminum borate and are hereby incorporated by reference.

As disclosed in Zletz U.S. Pat. No. 4,729,979, copper aluminum borate ($Cu_{2-x}Al_{6-y}B_4O_{17}M_mM'_nM''_y$ wherein M is a divalent metal, M' is a monovalent metal, m ranges from 0 to 0.8, n ranges from 0 to 16, X ranges from 0 to 8 and is equal to the sum of m+n/2, M" is a trivalent metal and y ranges from 0 to 1.2) which is at least partially reducible with hydrogen under Temperature Programmed Reduction conditions at a temperature no more than 50° C., preferably having a surface area of at least 5 $m^2$ per gram and a pore volume of at least 0.04 cc per gram, is a new catalyst and further that copper aluminum borate can be treated with a reducing agent to form a catalyst comprising finely divided metallic copper (zero valent copper) on a support comprising an aluminum borate. Part of the copper in the copper aluminum borate reacts with a reducing gas at relatively low temperature (about 175° to 350° C.) to form finely divided copper on the aluminum borate support.

When copper aluminum borate is used as a catalyst in the dehydrogenation of organic compounds or in a reaction medium containing a reducing gas, at least part of the copper in the copper aluminum borate is converted into finely divided copper on an aluminum borate support. In some reactions, such as in the dehydrogenation of alkylaromatics to alkenylaromatics, substantially all of the copper in the still active catalyst can be present as finely divided copper metal on an aluminum borate support, i.e., in the aluminum borate matrix. In other cases, the active catalyst always contains some copper aluminum borate. If part of the copper in copper aluminum borate is replaced with another divalent metal for example zinc or nickel, copper in the compound is still reducible to metallic copper at relatively low temperature.

While it is not clear at this point whether copper aluminum borate or copper on aluminum borate or combinations of the two is the true catalyst in dehydrogenation reactions and reactions employing a reducing gas, it has generally been found that the induction period for carrying out these reactions is reduced by treating the copper aluminum borate with a reducing agent such as cumene prior to the desired reaction to produce finely divided metallic copper on an aluminum borate support.

If neat copper aluminum borate having the empirical formula $Cu_2Al_6B_4O_{17}$ is viewed as having the structure $3Al_2O_3.2CuO.2B_2O_3$, the reduction with CO or $H_2$ can be represented in its simplest terms as follows:

$Al_2O_3.2CuO.2B_2O_3 + 2H_2 \rightarrow 3Al_2O_3.2B_2O_3 + 2Cu + 2H_2O$ $3Al_2O_3.2CuO.2B_2O_3 + 2CO \rightarrow 3Al_2O_3.2B_2O_3 + 2Cu + 2CO_2$ X-ray diffraction patterns of the products indicate that the aluminum borate crystal has the formula $2Al_2O_3.B_2O_3$ and that part of the $B_2O_3$ in the original copper aluminum borate crystal has been driven off and/or is present in the amorphous state. Partial replacement of the copper in copper aluminum borate with other divalent metals does not appear to interfere with the reduction of the copper to zero valent copper.

Unreduced copper aluminum borates (CuAB) have a distinguishing crystalline structure while substantially fully reduced CuAB (Cu on AB) has a different related crystalline structure as evidenced by the significant lines of their X-ray diffraction patterns. The 5.29 line has arbitrarily been set at 100 for Cu on AB in order to facilitate a comparison with ASTM data for such materials as CuAB and aluminum borate. The X-ray diffraction patterns in Table I show the significant lines for unreduced CuAB of this invention, substantially fully reduced CuAB (copper on aluminum borate) of this invention, $Al_4B_2O_9$ and copper.

X-ray data were determined by standard techniques. The radiation was the K-alpha double of copper, and a proportional counter spectrometer with a strip chart pen recorder was used. The peak heights, I, and the positions as a function of 2 times theta, where theta is the Bragg angle, were read from the spectrometer chart. From these the relative intensities, 100 $I/I_0$, where $I_0$ is the intensity of the strongest line or peak, and d (obs.), the interplanar spacing in A, corresponding to the recorded lines, were calculated. In Table I the relative intensities are given in terms of the symbols VVS=very very strong (over 100), VS=very strong (80-100), S=strong (50-80), M=Medium (20-50), W=weak (10-20) and VW=very weak (<10).

TABLE I

| dA | Cu on AB | Cu AB | Uhlig Cu AB | $Al_4B_2O_9$ | Cu |
|---|---|---|---|---|---|
| 7.50 ± .1 | | VW-M | M | | |
| 5.29 ± .05 | VS | VS | VS | VS | |
| 5.00 ± .05 | | S | S | | |
| 4.92 ± .03 | W-M | | | W | |
| 3.73 ± .03 | | W-M | W | | |
| 3.64 ± .03 | | VW-W | VW | | |
| 3.58 ± .03 | VW-M | | | VW | |
| 3.35 ± .03 | VW-M | W | W | M | |
| 2.98 ± .03 | | VW-W | W | | |
| 2.84 ± .03 | | VW-W | VW | | |
| 2.78 ± .02 | VW | | | | |
| 2.64 ± .02 | M | M-S | M | M | |
| 2.61 ± .02 | | W-M | W | | |
| 2.50 ± .02 | | W-M | VW | | |
| 2.45 ± .02 | W-M | | | W | |
| 2.26 ± .02 | | W-M | W | | |
| 2.22 ± .02 | W | | | VW | |
| 2.16 ± .02 | | M | W | | |
| 2.13 ± .02 | M | | | W-M | |
| 2.07 ± .02 | VVS | M | M | W | S |
| 1.97 ± .02 | VW-W | M | W-M | | |
| 1.91 ± .02 | VW | | VW | VW | |
| 1.86 ± .01 | | W-M | VW | | |
| 1.81 ± .01 | VVS | M | W | | M |
| 1.76 ± .01 | | VW | VW | | |
| 1.67 ± .01 | W | W-M | W | | |
| 1.60 ± .01 | | W-VW | VW | | |
| 1.555 ± .01 | W | W-VW | VW | W | |

As indicated above, the substantially fully reduced copper aluminum borate X-ray diffraction lines correspond primarily to the X-ray diffraction lines of the $Al_4B_2O_9$ and copper.

The significant X-ray diffraction lines for copper aluminum borate are set forth below in Table A.

TABLE A

| dA | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

As disclosed in Satek, part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel and magnesium have been successfully incorporated into copper aluminum borate crystals and, accordingly, X in the above formula can range from about 0.01 to 0.8, preferably about 0.05 to 0.50. Trivalent metal ions can appear as M" in the above formula, e.g., $Fe^{+++}$. However, chromium forms a chromite and appears to not to replace aluminum.

If desired, non-volatile cations such as alkali metal (M' in the above formula) or alkaline earth metal cations can be present during the preparation of the copper aluminum borate.

For purposes of this invention the term "aluminum borate" is used in the generic sense to be inclusive of all aluminum borate compounds, such as pure or neat aluminum borate, copper aluminum borate, zinc aluminum borate, etc. "Copper aluminum borate" is used in the generic sense to be inclusive of all compounds containing divalent copper, trivalent aluminum and borate, comprising the X-ray diffraction pattern of $Cu_2Al_6B_4O_{17}$, such as pure or neat copper aluminum borate, copper zinc aluminum borate, aluminum borate/copper aluminum borate, copper aluminum borate/copper chromite, copper aluminum borate/alumina, etc.

Briefly, the copper aluminum borate catalyst or zero valent copper on a support comprising aluminum borate for use in the dehydrocyclization process of the present invention can be prepared either from a gelled precursor in a liquid medium as disclosed in commonly assigned Zletz U.S. Pat. No. 4,729,979, incorporated herein by reference, or from a dry-mixed precursor as disclosed in commonly assigned U.S. Ser. No. 924,064, incorporated by reference. Regardless of which technique is used, preparation of the catalyst generally involves a three-step procedure comprising: (1) combining a source of divalent copper, trivalent aluminum and boron in the form of the oxide or borate, (2) drying the composition where necessary to remove water or diluent and (3) calcining the composition at a temperature sufficiently high to form crystalline copper aluminum borate having an X-ray diffraction pattern for $Cu_2Al_6B_4O_{17}$ as set forth in Table A.

In either the dry or liquid preparation of copper aluminum borate, suitable sources of copper include copper nitrate, copper acetate, copper carbonate, copper borate, basic copper carbonate ($CuCO_2 \cdot Cu(OH)_2$), copper acetate monohydrate, copper oxides and copper metal. Copper acetate monohydrate is preferred in the dry preparation. Suitable sources of boron include any solid boron containing reagent. Examples are boric acid, copper borate, aluminum borate, boron oxides, ammonium borate, ammonium hydrogen tetraborate, etc. Suitable sources of aluminum are alumina sols, aluminum nitrate, alumina, aluminum acetate, aluminum borate, etc. These components can be combined in approximately stoichrometric proportions to provide copper aluminum borate having the empirical formula $Cu_2Al_6B_4O_{17}$.

The preparation of copper aluminum borate for use in the present invention can be carried out by the liquid or gel technique described in Zletz. Using this technique, it is generally desirable to combine divalent copper, boron in the form of the oxide or borate ion, and trivalent aluminum in the form of aluminum salts or alumina in an aqueous medium. In order to avoid the introduction of any extraneous ions in the crystalline copper aluminum borate, it is generally desirable to avoid the presence of cations or anions that are not destroyed and/or volatilized during the subsequent drying and/or calcination step. The presence of volatile components in preparation of copper aluminum borate, such as water, $NH_3$, acetate ion, nitrate ion, etc., is advantageous in providing the copper aluminum borate with relatively high surface area and porosity desirable for most catalytic reactions. It is generally preferred to include ammonium salts or ammonium hydroxide in the above aqueous preparation to achieve the desired high surface area and porosity in the final catalyst.

Alternatively, copper aluminum borate catalyst useful in the present invention can be conveniently prepared using a solid-state method as disclosed in De Simone et al. commonly assigned co-pending U.S. Ser. No. 924,064, incorporated herein by reference. The solid-state preparation obviates the time-consuming and economically costly step of drying the catalyst precursor prior to calcining.

Briefly, the solid-state preparation of copper aluminum borate comprises (1) dry-mixing powdered reagents comprising suitable precursors of copper oxide (CuO), aluminum oxide ($Al_2O_3$), and boron oxide ($B_2O_3$) with at least about 3 wt % on a dry solids basis of a suitable solid binder to form a superficially dry copper aluminum borate precursor; (2) compacting the dry pre-cursor; and (3) calcining the precursor at a sufficiently high temperature to form crystalline copper aluminum borate. The terms "dry," "dry-mixed," "solid state," "solid" and, "superficially dry" are intended to denote conditions, processes, or reagents which are essentially free of liquid materials. These terms are not intended to exclude the presence of ambient atmospheric moisture or the water of hydration, in solid reagents. The terms "pre-cursor," "copper aluminum borate precursor," "dry-mixed precursor," etc., denote compositions which, upon calcination at a sufficiently high temperature, result in crystalline copper aluminum borate.

In the dry preparation, the solid reagents comprising suitable precursors of copper aluminum borate should be ground to a powder, individually or as a combination, through a 0.25 mm screen in a high speed grinder.

It is important that similar particle sizes of all reagents be attained in order that the solid state reaction to form crystalline copper aluminum borate proceeds as uniformly as possible upon calcination. Following grinding, a superficially dry mixture is prepared by combining the powdered dry reagents with about 3-20 wt % of a suitable solid binder.

A suitable solid binder is one which is capable of holding the powdered reagents together following compaction in a pellet press or extrusion apparatus, and which will burn away upon calcination, thus imparting porosity to the pellet. Preferred binders are solid stearins and the like, graphite, or mixtures thereof. Sterotex, a commercially available vegetable stearin, is particularly well suited as it burns off at a lower temperature than graphite and results in a better catalyst. The preferred amount of binder is at least about 3% by weight of the powdered reagents on a dry solids basis, but up to about 20% may be employed. About 5 wt. percent of the binder is recommended. The binder material can be combined with the powdered reagents using a conventional mixing apparatus for a period of about 10 to about 60 minutes. After the above-prescribed mixing of the powdered reagents and solid binder is completed, the resulting superficially dry mixture can be either extruded or pelletized using conventional techniques and apparatus.

In either the liquid or solid state preparation part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel, and magnesium have been substantially incorporated into copper aluminum borate crystals and accordingly X in the above formula can range from about 0.01 to 0.8, preferably about 0.05 to 0.50. Trivalent metal ions can appear as M" in the above formula, e.g., $Fe^{+++}$. However, chromium forms a chromite and appears not to replace aluminum. In addition, non-volatile cations such as alkali metal (M" in the above formula) or alkaline earth metal cations can be present during the preparation of the copper aluminum borate.

The catalyst precursor prepared by either of the methods described above should be calcined at a temperature in the range of from about 6500 to about 10000, preferably at least about 800° C. for about 1 to 24 hours, typically in air. The higher the calcination temperature, the shorter the calcination time. Calcinations below about 800° C. tend to provide a catalyst which has low activity for the cyclization reaction of the present invention. Other things being equal, the higher the calcination temperature the lower the surface area and porosity of the copper aluminum borate. Thus, at calcination temperatures exceeding 1000° C. the catalytic activity of the resultant material is substantially diminished. In the present invention the copper aluminum borate precursor mixture is initially calcined at a temperature of about 200° to 400° C., preferably about 300° C. for 3-4 hours to burn off volatiles, following which the temperature is increased to preferably between 780° and 860° C. for about 3-8 hours. The preferred calcining regime is 820° C. for about 4 hours.

Copper aluminum borate can be treated with any of the metals or metal compounds conventionally used in catalysis. Any one or more of the transition metals or compounds can be utilized such as the metals of Groups IB, IIB, IIIB, IVB, VB, VIB, VIIB and VIII of the Periodic Table. Suitable metals include zinc, cadmium, copper, silver, chromium, molybdenum, scandium, tungsten, manganese, titanium, rhenium, iron, cobalt, nickel, ruthenium, rhodium, palladium, osmium, iridium, vanadium, platinum, etc. These metals can be present in a concentration of from 0.01 to 30% by weight of the copper aluminum borate catalyst or copper on aluminum borate. These metals or metal compounds can be applied as salts, oxides, etc., and if desired, thermally decomposed to give the corresponding metal or oxides.

In accordance with the present invention, copper aluminum borate and zero valent copper on a support comprising aluminum borate can be used to cyclize or dehydrocyclize a wide variety of starting compounds. In general, compounds suitable for cyclization in the present invention are those having a fragment in which a carbon containing chain of at least three atoms in sequence is bonded at one end to nitrogen, oxygen or sulfur where the latter are bonded to at least one hydrogen atom. Without limitation, the following are examples of cyclization starting compounds, and the products resulting from the cyclization thereof according to the present invention. The cyclization products have well known uses in perfumes, dyes, pharmaceuticals, flavorings, etc.

| Cyclization Product | Starting Compound | Uses |
|---|---|---|
| 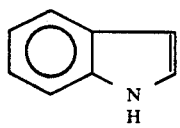 indole | 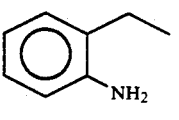 o-ethylaniline | used in the manufacture of: perfumes, dyes, tryptophan, anti-inflammatories, analgesics; precursor for plant growth hormones. |
| 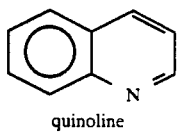 quinoline | 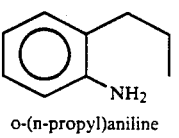 o-(n-propyl)aniline | solvents, dye intermediate; precursor to niacin. |
| 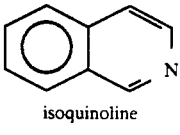 isoquinoline | 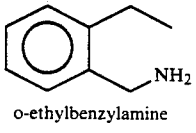 o-ethylbenzylamine | used in manufacture of: dyes; rubber accelerators antimalarials, insecticides. |
| 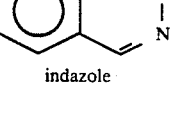 indazole | 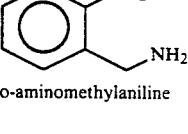 o-aminomethylaniline | |
| 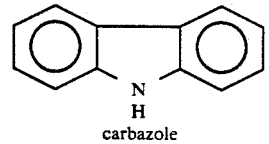 carbazole | 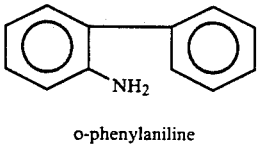 o-phenylaniline | dye intermediate; used in UV sensitive photographic plates; carbohydrate processing reagent. |
| 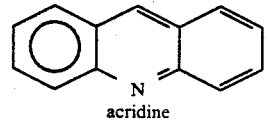 acridine |  o-benzylaniline | used in manufacture of: dyes, antiseptics (proflavine/acriflavine) |
| 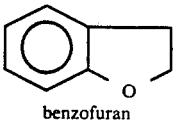 benzofuran | 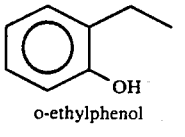 o-ethylphenol | polymers; coumarone-indene resins |
| 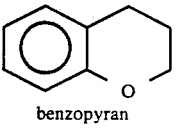 benzopyran | 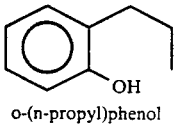 o-(n-propyl)phenol | |

| Cyclization Product | Starting Compound | Uses |
|---|---|---|
| benzothiophene | o-ethylthiophenol | used in manufacture of: pharmaceuticals, thioindigo |
| dibenzothiophene | o-phenylthiophenol | |
| phenothiazine | o-aminodiphenyl sulfide or | used in the manufacture of: insecticides, pharmaceuticals |
| phenothiazine | o-phenylaminothiophenol | |
| xanthene | o-benzylphenol | |

The cyclization process of the present invention is carried out by contacting in a reaction zone a starting compound meeting the definitions set forth in Summary of the Invention under appropriate conditions of temperature, flow rate of reactant, and carrier gas selection. The reaction can be conducted anywhere from about 400° C. to about 800° C. Any inert gas such as helium or nitrogen can be used as diluent carrier gas for the reaction. Weight hourly space velocities of 0.05 to 2.0, preferably 0.1 to 0.2, and molar diluent ratios from 1:1 to 100:1, preferably 8:1 to 20:1 can be used.

The present invention can be used to manufacture indole from o-ethylaniline. In this reaction the preferred conditions are as follows: (1) liquid flow rate: 2-10 ml/hr of 25 or 50% o-ethylaniline in benzene; (2) WHSV: 0.1 to 0.6; diluent ratio 8:1 to 19:1, preferably 11:1 to 14:1; (3) preferred diluent: nitrogen or benzene solvent; (4) reaction temperature 520° C. to 680°, preferably 580° to 650° C.

The conversion of o-ethylaniline to indole using copper aluminum borate catalyst is a gas phase dehydrocyclization. The major dehydrogenation and dehydrocyclization products are indole, indolene (2,3-dihydroindole) and o-vinylaniline. The predominant by-products of the reaction, produced through cracking, are aniline and o-toluidine. Much smaller amounts of other cracking and disproportionation compounds such as ethylbenzene, styrene, and methylindole isomers are found. Oxygen containing compounds are also detected, presumably formed in conjunction with a hydrolysis reaction. Examples are phenol, o-aminoacetophenone, benzofuran, and 2-cyanophenol. The amount of these products increases if steam is used as a diluent.

The present invention can also be used to manufacture benzofuran and benzofuran derivatives from ortho-alkylated phenols. Preferred conditions for this reaction are as follows: temperature: 500° C.-700°, preferably 550°-680° C. WHSV=0.1 to 0.5; inert diluents such as hydrocarbon solvents, nitrogen etc. Molar diluent ratios are preferably 8:1 to 20:1. If desired, hydrogen gas can be introduced to extend catalyst lifetime. Benzofuran is the major product of the reaction of o-ethylphenol; selectivity is 75-80%. The precursors to benzofuran, 2,3-dihydrobenzofuran (1-2%) and o-vinylphenol (2-15%) are also formed. Selectivity to these three products is 83-93%. The unwanted by-products phenol and o-cresol are produced through cracking reactions.

The following examples are intended for illustration purposes and are not intended to limit the invention as claimed.

EXAMPLE I

Solid state preparation of copper aluminum borate was carried out as follows: 40.4 gm of copper acetate (Cu(OAc)$_2$ H$_2$O), 25.0 gm of boric acid (H$_3$BO$_3$) and 40.0 gm of Amalo No. 15 alumina (77.5% Al$_2$O$_3$; 22.5% H$_2$O) were hand-mixed in a jar for 1 min. and then ground thoroughly through a 0.25 mm screen in a high speed grinder to assure that all reagents were ground to a similar particle size for uniform mixing. The ground reagents were then dry-mixed with 5 wt. percent finely ground Sterotex. Roller mixing of the Sterotex and the ground reagents was carried out for about 30 minutes. The resulting liquid free precursor mixture was then formed into ⅛-inch diameter by 3/16-inch length pellets using a Stokes Model 521-2 four-ton single-punch powder compacting press. Crush strength of the pellets was maintained between 4.5 and 6.0 pounds. An Ametek Accuforce Cadet (40-pound) force gauge was used to monitor crush strength of the pellets. The pelletized precursor was then calcined using the following calcination program: (1) gradual increase from 150° C. to 300° C. a rate of 90° C./hour requiring 2 hours; (2) 300° C. for 2 hours; (3) gradual increase from 300° C. to 820° C. at a rate of 130° C./hour requiring 4 hours; (4) 820° C. for 3 hours; and (5) gradually reduced from 820° C. to 150° C. over a period of about 10 hours.

EXAMPLE II

Copper aluminum borate as prepared in Example I was treated with 0.2% palladium as follows: 28 g of $Pd(NO_3)_2 \cdot H_2O$ was dissolved in 40 ml of de-ionized water. A syringe was used to evenly coat 62.2 g of copper aluminum borate pellets of Example I with the $Pd(NO_3)_2$ solution. The treated pellets were calcined as follows: (1) increase gradually from 120° C. to 300° C. over 2 hour period; (2) maintain at 300° C. for 3 hours; (3) gradually decrease from 300° C. to 120° C.

EXAMPLE III

Copper aluminum borate preparation was carried out in accordance with Examples I and II except that the copper aluminum borate was treated with 1.0 wt. % molybdenum (in the form of ammonium molybdate) instead of palladium.

EXAMPLE IV

Solid state preparation of copper aluminum borate incorporating molybdenum and palladium was carried out as follows: copper acetate, 36 g, boric acid, 22.3 g, Davison VFA alumina, 41.7 g, were mixed in a jar. Following mixing, ammonium molybdate, 1.8 g, and palladium (II) acetate, 0.42 g, were dry mixed with the copper aluminum borate precursor reagents. After all the reagents were mixed, the reagents were then ground for about 30 seconds through a 0.25 mm screen. To the milled mixture was added 5.11 g of Sterorex as binder followed by thorough dry-mixing of all the ingredients. The dry-mixed precursor mixture was then formed into pellets having a crush strength between 4.5 and 7.0 pounds. The pellets were calcined at 300° C. for about 3 to 4 hours and then at 820° C. for 8 hours.

EXAMPLE V

Solid state preparation of copper aluminum borate was carried out as follows: 161.4 g of copper acetate $(Cu(OAc)_2 \cdot H_2O)$, 100.0 g of boric acid $(H_3BO_3)$ and 186.8 g of Davison VFA alumina (68.4% $Al_2O_3$; 31.6% $H_2O$) were hand-mixed in a jar for 1 minute and then dry-mixed with 5 wt. % Sterorex and formed into pellets and calcined in accordance with Example I.

EXAMPLE VI

Example I was repeated using 10% Sterotex in the precursor preparation.

EXAMPLE VII

Preparation of $Cu_{1.798} Pd_{0.002} Ni_{0.200} Al_6B_4O_{17}$ was carried out as follows: 5.82 g of $Ni(NO_3)_2 \cdot 2\frac{1}{2} H_2O$ dissolved in 10 ml $H_2O$; 41.82 g of $Cu(NO_3)_2 \cdot 2\frac{1}{2} H_2O$ dissolved in 170 ml of $H_2O$; and 392.31 g of PHF alumina (7.8% $Al_2O_3$); and 24.73 g $H_3BO_3$ dissolved in 100 ml $H_2O$ were added to a blender and mixed at low speed for 1 minute resulting in a light blue, foamy mixture. To this mixture was added 5 ml of a palladium nitrate solution prepared by dissolving 0.168 g of $Pd(NO_3)_2 H_2O$ in 20 ml $H_2O$, followed by blending on low speed for 3 minutes. The appearance of the mixture did not change. pH was 4.8. 10 ml of $NH_4(OH)$ was added to the blender. Mixing was stopped after 15 seconds of blending on low speed. The resultant stiff gel (darker blue) was stirred with a spatula and blending was continued 2 more minutes. The gel (pH-5.0) was spread onto a tray to air dry overnight, followed by oven drying for 17 hours at 120° C., 20" Hg with a nitrogen purge. The oven dried sample was then calcined in air at 830° C. for 8 hours utilizing a four hour ramp up to 830° C. from 120° C. and a four hour ramp down from that temperature. The resultant catalyst had a BET surface area of 22 $m^2/g$; pore volume 0.079 cc/g; and pore radius of 49 Å.

EXAMPLE VIII

Preparation of copper aluminum borate having the formula $Cu_{1.998} Pd_{0.002} Al_6B_4O_{17}$ was carried out using the procedure of Example VII. The amounts of the reagents were as follows: 5 ml of a palladium nitrate solution prepared by dissolving 0.168 g of $Pd(NO_3)_2 \cdot H_2O$ in 20 ml of $H_2O$; 46.47 g of $Cu(NO_3)_2 \cdot 2\frac{1}{2} H_2O$ dissolved in 170 ml of $H_2O$; 392.31 g of PHF alumina sol (7.8% $Al_2O_3$); and 24.73 g $H_3BO_3$ dissolved in 100 ml of $H_2O$. The resulting catalyst had a BET surface area of 15 $m^2/g$, pore volume of 0.086 cc/g and pore radius of 79 Å.

EXAMPLE IX

Preparation of $Cu_{1.8} Ni_{0.2} Al_6B_4O_{17}$ was carried out as follows: 4.85 g $Ni(NO_3)_2 \cdot 2\frac{1}{2} H_2O$ dissolved in 10 ml $H_2O$; 326.92 g PHF alumina-sol (7.8% $Al_2O_3$); and 20.61 g $H_3BO_3$ dissolved in 100 ml of $H_2O$ were added to a blender. The mixture was first stirred with a spatula, then blended for 1 minute on low speed. The resulting sky blue, foamy liquid had a pH of ≅5.0. $NH_4OH$ (Mallinckrodt Analytical Reagent) was added to the mixture to cause gel formation. The $NH_4OH$ was first blended in with a spatula, then the mixture was blended for 1 minute on low speed. The mixture was checked and stirred with a spatula, then the blending process was continued for the remaining 50 seconds. The resulting substance was a deep sky blue color (ph∼6.0). The substance was scraped onto a plastic tray and was evenly distributed over the tray to air dry. 101.53 g of the air-dried material was oven-dried (120° C., 19" Hg, 20 hr, nitrogen purge) followed by calcining at 830° C. for 8 hours. The resulting catalyst had a BET surface area of 10 $m^2/g$, pore volume of 0.071 cc/g and pore radius 6.1 Å.

EXAMPLE X copper aluminum borate catalyst was prepared as follows: 100 g of boric acid was added to 960 ml of distilled $H_2O$ in a large beaker and dissolved by heating on a hot plate. In a separate beaker, 161.6 g of copper acetate $(Cu(OAC))_2 \cdot H_2O$ was added to 600 ml of moderately heated distilled $H_2O$. After the copper acetate was substantially dissolved (∼15 min.), 120 ml of $NH_4OH$ was added to assist dissolution of the copper acetate. Separately, 1.588 g of PHF alumina sol $(Al_2O_3)$ containing about 7.8% solids was poured into a large mixing apparatus, to which was added the hot boric acid solution followed by mixing at low speed with the top covered for about one minute. To the separate copper acetate solution was added an additional 120 ml of $NH_4OH$, at which point the copper salt was completely dissolved. The ammonia/copper acetate solution was then added gradually to the mixing apparatus containing the PHF alumina with mixing and stirring as needed. Throughout addition of the ammonia/copper acetate solution to the PHF alumina, hand stirring with a spatula was used to promote even formation of the gel which begins to form immediately upon addition of the copper solution to the alumina. Occasionally, the mixer was turned off in order that material collecting at the bottom of the mixer could be redistributed throughout the mixture. After all the copper solution was added, the gel was mixed at a moderate speed for about 5 minutes, until a smooth consistency was obtained. The gelled precursor was then spread out to dry for 1-2 days under a hood in a layer about 203 mm thick. The air dried catalyst was then collected in crystallizing dishes and placed in a vacuum oven overnight at a temperature of about 45° C. and with a nitrogen purge. Over a period of 2 additional days the vacuum oven temperature was raised gradually (10°-20° C.) until a temperature of 100°-100° C. was reached. The vacuum dried catalyst precursor was then transferred to alumina trays and calcined as follows: 120° C. to 300° C. gradually over 2 hours; 300° C. for 2 hours; 300° to 820° C. gradually over 3 hours; 820° C. for 3 hours; 820° to 120° C. gradually over 4 or more hours.

EXAMPLE XI

This example illustrates the preparation of a copper aluminum borate/copper chromite catalyst. Into a blender was placed 300.77 g of an alumina sol (9.73 dry wt. % $Al_2O_3$, 0.2869 moles $Al_2O_3$) and 23.64 g boric acid (0.38 moles) dissolved in 250 ml of water. A copper nitrate/chromium acetate solution was prepared by dissolving 53.34 g copper nitrate (0.22 moles) in 60 ml water and adding thereto a solution of 15.56 g chromium acetate in 70 ml distilled water. On heating, the copper nitrate/chromium acetate solution became dark and opaque. The dark opaque solution was added to the blender and thoroughly mixed before transfer to petri dishes to dry. The petri dishes were placed in a vacuum oven and dried overnight at 55° C. at 20 inches (0.3 atm) vacuum. Over the next two days, the temperature was gradually raised to 106° C. while the vacuum pressure was increased to about 15 inches (0.5 atm), yielding 110.67 g of a dark blue solid. A portion of this material (27.09 g) was placed in a petri dish and calcined by heating as follows: 120° C. for 0.6 hr, 235° C. for .5 hr, 250° C. for .5 hrs, 375° C. for 0.8 hr, and then 400° C. After cooling for 1 hr the composition while still at 300° C. was placed in a desiccator overnight. The solid (13.76 g) was placed in a small alumina dish and calcined according to the following program: 40° C. for 2 hrs, 500° C. for 1 hr, 500° C. for 1.5 hrs, 735° C. for 3 hrs and then held at 750° C. and cooled. After cooling for 1.2 hrs, the temperature reached 482° C. and the dish was removed from the oven and placed in a desiccator, yielding 13.48 g of 11.2% copper chromite in copper aluminum borate.

EXAMPLE XII

A hot solution of 21.63 g boric acid in 225 ml distilled water was added to 294.44 g of alumina sol (27.03 g alumina on a dry solids basis) in a blender while mixing. To this was added 31.43 g copper acetate and 4.35 g nickel acetate in 50 ml distilled water and 38 ml concentrated ammonium hydroxide. The solid salts remaining in the beaker were dissolved in 20 ml concentrated ammonium hydroxide and added to the blender. The beaker was then rinsed with distilled water and added to the blender. The stiff mixture was worked with a spatula and the blender action until a smooth gel was produced. The gel was transferred into plastic dishes for drying. After three days, the solids were transferred to two petri dishes and vacuum dried for 48 hours (0.25 arm, 50° C. initial temperature and 106° C. final temperature). Sixteen and seventeen hundredths g of the dry solids were calcined by heating from 115° C. to 260° C. for a 2 hr period, held at 260° C. for 1 hr, from 260° C. to 820° C. over a 3 hr period, held at 820° C. for 3 hrs and then cooled to 110° C. X-ray diffraction data indicated that the material was highly crystalline and had only a single component. The copper (90) nickel (10) aluminum borate had a surface area of 36 square meters per gram, 0.1289 ccs per gram pore volume and an average pore radius of 43 Å.

EXAMPLE XIII

A hot solution of 23.05 g boric acid in 240 ml distilled water was added to 310.94 g alumina sol (28.52 g dry solids basis) in a blender while mixing. To this were added 40.54 g copper nitrate and 5.55 g zinc nitrate in 50 ml distilled water. Concentrated ammonium hydroxide (60 ccs) was then added and the mixture blended using a spatula until it was very smooth. The gel was placed on a tray and allowed to dry in air for 48 hrs and then dried under vacuum at 91° C. A portion of this solid was calcined at 380° C. to decompose nitrates and then at 825° C. for 3 hours. The copper (90) zinc (10) aluminum borate was highly crystalline and X-ray diffraction indicated that it was homogeneous. The material had a surface area of 35 square meters per gram, 0.1411 cc/g pore volume and an average pore radius of 59 Å.

EXAMPLE XIV

This example illustrates the preparation of a large batch of copper aluminum borate. The copper aluminum borate was prepared by
1) adding 400 g $H_3BO_3$ to 3384 ml distilled water and heating to dissolve;
2) adding 646.4 g $Cu(OAc)_2.H_2O$ to 2400 ml water. Heating and stirring to substantially dissolve. After 15 minutes of heating adding one-half (480 ml) 29% aqueous $NH_3$ to speed dissolution of salt;
3) weighing 6352 g PHF alumina (7.8% solids) to mixer bowl;
4) adding hot boric acid solution to the PHF alumina in a mixer. Mixing slowly for 1 minute;
5) adding remaining 480 ml (295 aqueous ammonium hydroxide) ammonia to $Cu(OAc)_2$ solution.
6) after all solids were dissolved adding the ammoniacal copper acetate solution to the slowly mixing liquid in the blender forming a gel. Increasing the mixing speed and thoroughly mixing the gel for −5 minutes;
7) removing the smooth uniform consistency gel from the mixer, and spreading to dry on large plastic sheets in layer −⅛" thick, for two days;
8) collecting the air-dried catalyst (now shriveled into random sized flakes), placing in crystallizing dishes and loading into a vacuum oven under 20" of house vacuum (maintained with $N_2$ bleed) at 45° C. overnight;
9) raising the vacuum oven temperature 10°-20° C. at a time at intervals over a period of two additional days until 100°-110° C. is reached;

10) transferring the vacuum dried catalyst to alumina trays, then placing in a calcining over at 120° C. Calcination was as follows:

| 120° C. → | 2 hrs |
|---|---|
| 300° C | 2 hrs |
| 300° C. → | 3 hrs |
| 820° C | 3 hrs |
| 820° C. → | >4 hrs |

In the following examples demonstrating cyclization according to the present invention, the reactions were carried out in a gas-phase flow-through fixed-bed reactor. Reactors were ⅜ inch O.D. by 21 inch quartz tubes fitted with a ¼ inch thermowell; catalyst frit was located approximately 1 inch below center. This allowed catalyst to be loaded in such a way as to minimize empty reactor space in the hottest reactor zones. Heat was provided by single zone Lindberg furnaces regulated by standard on-site controllers. Liquid reactants were fed and regulated by Harvard syringe pumps. Gaseous reactants were regulated with micrometering valves, measured by gas bubble meters. Liquid products were collected in a series of traps employing water/ice, dry ice/acetone, and a water-cooled spiral condenser; gaseous products were not collected. Reactants and products were identified and quantified by gas chromatographic analysis on a Hewlett-Packard 5790 fitted with an OV 225 6 foot×¼ inch packed glass column. Product identities were determined and confirmed by comparison with authentic samples and by GC-mass spectroscopy analysis. Response factors were determined for o-ethylaniline, indole, and indolene. Product concentrations reported have been calculated from area percent data.

EXAMPLE XV

Copper aluminum borate (7 g) prepared in accordance with Example I was loaded into the quartz tube reactor of the reactor system outlined above. The catalyst was optionally pre-reduced with cumene for 24 hours (20:1 diluent ratio-17:1 steam, 3:1 nitrogen, at 0.81 liquid hour space velocity and temperature of 600° C.). O-ethylaniline (25 wt. % in benzene) was fed to the reactor at WHSV of 0.1. Diluent was provided by nitrogen carrier gas set at 45 cc/min. Diluent ratio was 20:1. The reaction temperature was 580° C. Conversion was 85%; selectivity was 86–88% indole plus indolene (ratio of indole to indolene=12:1). Aniline through cracking represented 5% of the total products with 7–9% unidentified by-products.

EXAMPLE XVI

Example XV was repeated except the diluent ratio was 12:1, WHSV=2. Conversion was 93%; selectivity was 84–88% (Indole:Indolene=20:1). After 200 hours on stream conversion was 90-95%, selectivity 86%+4%. No deactivation was noted at 200 hours.

EXAMPLE XVII

The basic procedure outlined in Example XV was repeated using 6.6 g of copper aluminum borate from Example V and o-ethylphenol in toluene as the feed. WHSV was 0.15 and the diluent ratio was 20:1. The diluent was nitrogen. The reaction was conducted at 600° C. Conversion was 31% with selectivity to benzofuran or its precursors of 86%: benzofuran, 71%; 2,3-dihydrobenzofuran, 2%; o-vinylphenol, 13%; other, 14%.

EXAMPLE XVIII

Example XVII was repeated at 630° C. Conversion was with a total selectivity of 86% (benzofuran 78%).

EXAMPLE XIX

Example XVII was repeated at 650° C. Conversion was selectivity to benzofuran, 80%.

EXAMPLE XX

In Table 1, below, dehydrocyclization of o-ethylaniline to indole over copper aluminum borate prepared in the preceding examples is compared with commercial iron oxide and platinum on aluminum catalysts. The reactions summarized in the table were run using the reactor system and procedures of the preceding examples. Conditions were as follows: WHSV, 0.1; molar diluent ratio, 13/1; catalyst age, 30–40 hours. Selectivity was calculated by adding indole+indolene+o-vinylaniline.

TABLE 1

| Catalyst | Temp °C. | Conv. | Sel | Indole | Indolene |
|---|---|---|---|---|---|
| Example I | 580 | 85 | 90 | 83 | 6 |
|  | 610 | 93 | 90 | 85 | 3 |
|  | 650 | 100 | 84 | 82 | — |
|  | 630 | 97 | 86 | 84 | 1 |
| Example V | 590 | 78 | 83 | 75 | 6 |
|  | 630 | 89 | 84 | 78 | 3 |
|  | 650 | 95 | 77 | 72 | 1 |
| Example VI | 620 | 58 | 84 | 70 | 12 |
|  | 630 | 74 | 83 | 74 | 6 |
|  | 650 | 93 | 79 | 74 | 2 |
| Example VII | 580 | 22 | 72 | 22 | 46 |
|  | 630 | 66 | 62 | 40 | 18 |
|  | 650 | 83 | 61 | 42 | 11 |
| Example II | 580 | 62 | 90 | 74 | 15 |
|  | 630 | 95 | 89 | 85 | 2 |
| iron-oxide catalyst | 630 | 59 | 78 | 59 | 16 |
| Pt/alumina catalyst | 550 | 83 | 85 | 80 | 5 |
|  | 590 | 97 | 89 | 88 | 1 |
|  | 630 | 99 | 89 | 86 | 1 |

| Catalyst | o-vinyl aniline | Aniline | o-tol-uidine | Other |
|---|---|---|---|---|
| Example I | 1 | 4 | 2 | 6 |
|  | 2 | 4 | 2 | 7 |
|  | 2 | 9 | 4 | 2 |
|  | 1 | 5 | 3 | 8 |
| Example V | 2 | 8 | 6 | 4 |
|  | 3 | 9 | 6 | 3 |
|  | 4 | 12 | 6 | 6 |
| Example VI | 2 | 8 | 5 | 3 |
|  | 3 | 9 | 6 | 3 |
|  | 3 | 11 | 6 | 4 |
| Example VII | 4 | 12 | 8 | 7 |
|  | 4 | 14 | 11 | 11 |
|  | 8 | 17 | 11 | 9 |
| Example II | 1 | 4 | 3 | 4 |
|  | 2 | 5 | 4 | 3 |
| iron-oxide catalyst | 3 | 12 | 2 | 8 |
| Pt/alumina catalyst | — | 7 | 3 | 6 |
|  | — | 6 | 2 | 3 |
|  | 2 | 8 | 2 | 2 |

EXAMPLE XXI

The effects of varying WHSV in the dehydrocyclization of o-ethylaniline to indole over copper aluminum borate are summarized in Table 2 below.

TABLE 2

| Catalyst | WHSV | Conv. | Sel | Indole | Indolene |
|---|---|---|---|---|---|
| Example I | 0.10 | 98 | 89 | 87 | 1 |
|  | 0.16 | 83 | 87 | 81 | 4 |
|  | 0.22 | 79 | 85 | 76 | 7 |
|  | 0.30 | 59 | 86 | 68 | 16 |
|  | 0.45 | 54 | 85 | 63 | 20 |
| Example V | 0.10 | 85 | 83 | 77 | 4 |
|  | 0.16 | 63 | 81 | 68 | 11 |
|  | 0.22 | 51 | 81 | 62 | 17 |
|  | 0.30 | 42 | 80 | 54 | 24 |
| Example II | 0.10 | 79 | 80 | 71 | 7 |
|  | 0.16 | 70 | 77 | 64 | 11 |
|  | 0.22 | 64 | 72 | 55 | 13 |
|  | 0.30 | 57 | 74 | 52 | 18 |

| Catalyst | o-vinyl aniline | Aniline | o-tol- uidine | Other |
|---|---|---|---|---|
| Example I | 1 | 4 | 2 | 6 |
|  | 2 | 4 | 3 | 6 |
|  | 2 | 5 | 4 | 5 |
|  | 2 | 6 | 4 | 4 |
|  | 2 | 7 | 4 | 4 |
| Example V | 2 | 8 | 5 | 4 |
|  | 2 | 9 | 6 | 4 |
|  | 2 | 9 | 6 | 4 |
|  | 2 | 9 | 7 | 4 |
| Example II | 2 | 7 | 6 | 6 |
|  | 3 | 8 | 6 | 8 |
|  | 4 | 10 | 8 | 8 |
|  | 4 | 11 | 9 | 6 |

Note: Conditions are: 630° C., molar diluent ratio 13/1 to 1; catalyst age 30-40 hours. Selectivity is calculated by adding indole + indolene + o-vinylaniline.

EXAMPLE XXII

Table 3 below summarizes the effects of varying diluent ratio upon dehydrocyclization of o-ethylaniline to indole over copper aluminum borate.

TABLE 3

| Catalyst | Diluent Ratio (Mole) | Sel |
|---|---|---|
| Example I | 8/1 | 85 |
|  | 9/1 | 86 |
|  | 11/1 | 85 |
|  | 12/1 | 87 |
|  | 13/1 | 87 |
|  | 19/1 | 89 |

Note: Conditions are WHSV = 0.2, temperature 630° C., catalyst age 30-40 hours. Selectivity is calculated by adding indole + indolene + o-vinylaniline.

EXAMPLE XXII

Table 4 below compares the effect of catalyst age on dehydrocyclization of o-ethylaniline to indole for copper aluminum borate and for commercial iron oxide and platinum on alumina catalysts.

TABLE 4

| Catalyst | Catalyst Age (hours) | Conv. | Sel | Indol | Indolene |
|---|---|---|---|---|---|
| Example I | 50 | 97 | 87 | 85 | 1 |
|  | 100 | 98 | 89 | 87 | 1 |
|  | 150 | 96 | 90 | 88 | 1 |
|  | 200 | 89 | 88 | 84 | 3 |
|  | 250 | 94 | 87 | 84 | 2 |
|  | 300 | 93 | 89 | 86 | 2 |
|  | 400 | 91 | 86 | 81 | 4 |
| iron-oxide catalyst | 10 | 60 | 77 | 58 | 17 |
|  | 20 | 68 | 58 | 37 | 18 |
|  | 35 | 71 | 78 | 63 | 11 |
|  | 45 | 42 | 83 | 58 | 23 |
| Pt/alumina catalyst | 20 | 100 | 91 | 89 | — |
|  | 30 | 96 | 88 | 85 | 2 |
|  | 40 | 80 | 84 | 73 | 9 |
|  | 50 | 59 | 74 | 57 | 15 |

| Catalyst | o-vinyl aniline | Aniline | o-tol- uidine | Other |
|---|---|---|---|---|
| Example I | 1 | 4 | 2 | 7 |
|  | 1 | 4 | 2 | 6 |
|  | 1 | 4 | 2 | 4 |
|  | 1 | 4 | 3 | 6 |
|  | 1 | 3 | 2 | 8 |
|  | 1 | 4 | 2 | 6 |
|  | 1 | 6 | 5 | 3 |
| iron-oxide catalyst | 2 | 11 | 2 | 10 |
|  | 3 | 40 | 2 | — |
|  | 4 | 12 | 3 | 7 |
|  | 2 | 10 | 2 | 5 |
| Pt/alumina | 2 | 6 | 1 | 2 |
|  | 1 | 6 | 4 | 3 |
|  | 2 | 7 | 6 | 4 |
|  | 2 | 11 | 10 | 5 |

Note: Conditions: WHSV 0.1-0.15; molar diluent ratio 13/1; temperature 630° C. (Pt. on alumina 590° C.). Selectivity is calculated by adding indole + indolene + o-vinylaniline.

We claim:

1. A cyclization process utilizing the catalyst copper aluminum borate which comprises the step of contacting (1) a compound having a fragment in which a carbon-containing chain of at least three atoms in sequence is bonded at one end thereof to a nitrogen, oxygen, or sulfur atoms, and at the opposite end to a carbon, nitrogen, oxygen, of sulfur atom, where the latter are bonded to at least one hydrogen atom; with (2) a catalyst consisting essentially of at least one member selected from the group consisting of (a) crystalline copper aluminum borate having the significant x-ray diffraction lines set forth in Table A and (b) zero valent copper on a support comprising at least one member selected from the group consisting of $Al_4B_2O_9$ and said crystalline copper aluminum borate, the zero valent copper on the support being formed by the reduction of the crystalline copper aluminum borate, said cyclization process being conducted under conditions sufficient to effect ring closure between the ends of the fragment to obtain a compound comprising a heterocyclic ring.

2. The cyclization process of claim 1 wherein said chain of at least three atoms in sequence consists essentially of carbon atoms.

3. The cyclization process of claim 2, said chain having an —$NH_2$ group bonded at one end thereof.

4. The cyclization process of claim 2, said chain having an —OH group bonded at one end thereof.

5. The cyclization process of claim 2, said chain having an —SH group bonded at one end thereof.

6. The cyclization process of claim 2 wherein said chain includes two contiguous carbon atoms constituting two adjacent carbons of a ring moiety.

7. The cyclization process of claim 6 wherein said ring moiety comprises a benzene ring.

8. The cyclization process of claim 6 wherein said chain of at least three atoms in sequence has bonded at one end thereof an —$NH_2$ group.

9. The cyclization process of claim 6 wherein said chain of at least three atoms in sequence has bonded at one end thereof an —OH group.

10. The cyclization process of claim 6 wherein said chain of at least three atoms in sequence has bonded at one end thereof an —SH group.

11. The cyclization process of claim 8 wherein the heterocyclic compound formed is indole.

12. The cyclization process of claim 9 wherein the heterocyclic compound formed is benzofuran.

13. The cyclization process of claim 10 wherein the heterocyclic compound formed is benzothiofuran.

14. A cyclization process utilizing copper aluminum borate catalyst which process comprises the step of contacting (1) a starting compound comprising at least one five- or six-membered ring having ring substituents comprising (a) a first substituent selected from (i) a methyl group and (ii) a hydrocarbyl-containing group comprising a continuous sequence of two or more atoms, said sequence having a first atom selected from carbon, nitrogen, oxygen and sulfur bonded directly to the ring, and a second atom selected from carbon, nitrogen, oxygen and sulfur, having at least one hydrogen atom bonded thereto and separated by not more than one sequence atom from said first atom; and (b) a second substituent ortho to the first and comprising nitrogen, oxygen, or sulfur bonded directly to the ring or separated therefrom by a continuous sequence of not more than two atoms; with (2) a catalyst consisting essentially of at least one member selected from the group consisting of (a) crystalline copper on a support comprising at least one member selected from the group consisting of $Al_2B_2O_9$ and said crystalline copper aluminum borate, the zero valent copper on the support being formed by the reduction of the crystalline copper aluminum borate, said cyclization process being conducted under conditions sufficient to effect ring closure between said first and second substituents resulting in formation of a heterocyclic ring fused to the ring of the starting compound.

15. The cyclization process of claim 14 wherein the ring of the starting compound is a five-membered ring.

16. The cyclization process of claim 14 wherein the ring of the starting compound is a six-membered ring.

17. The cyclization process of claim 16 wherein the ring is aromatic.

18. The cyclization process of claim 16 wherein said first substituent is selected from category (ii) of claim 1, said substituent being $C_2$ to $C_{20}$ hydrocarbyl.

19. The cyclization process of claim 18 wherein said second substituent comprises —NRR, —OR, or —SR bonded directly to the ring of the starting compound or separated therefrom by a straight chain of carbons no greater than two carbons in length, where R is H or lower alkyl.

20. The cyclization process of claim 19 wherein ring closure results in formation of a five membered heterocyclic ring fused to the ring of the starting compound.

21. A cyclization process utilizing the catalyst copper aluminum borate which comprises the step of contacting (1) a starting compound having a fragment characterized by the general formula A or B below:

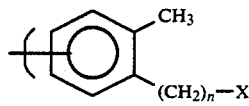

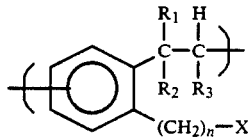

wherein $R_1$, $R_2$ and $R_3$, the same or different, are H or $C_1$ to $C_8$ hydrocarbyl and where $R_2$ and $R_3$ can be separate substituents or joined such that $R_2$, $R_3$, $C_1$ and $C_2$ constitute a ring; X is —NRR, —OR or —SR, such that the R groups, the same or different, are H or $C_1$ to $C_8$ hydrocarbyl and n=0 to 2; with (2) a catalyst consisting essentially of at least one member selected from the group consisting of (a) crystalline copper aluminum borate having the significant x-ray diffraction lines set forth in Table A and (b) zero valent copper on a support comprising at least one member selected from the group consisting of $Al_4B_2O_9$ and said crystalline copper aluminum borate, the zero valent copper on the support being formed by the reduction of the crystalline copper aluminum borate, said cyclization process being conducted under conditions sufficient to effect ring closure between the substituent ortho to one another of general formula A and B, resulting in formation of a heterocyclic ring fused to the ring of the starting compound.

22. The cyclization process of claim 21 wherein the starting compound has the general formula A, where n=1 or 2.

23. The cyclization process of claim 21 wherein the starting compound has the general formula B, where n=0.

24. The cyclization process of claim 23 wherein X is —$NH_2$.

25. The cyclization process of claim 23 wherein X is —OH.

26. The cyclization process of claim 23 wherein X is —SH.

27. The cyclization process of claim 24 wherein the heterocyclic compound formed is indole.

28. The cyclization process of claim 25 wherein the heterocyclic compound formed is benzofuran.

29. The cyclization process of claim 26 wherein the heterocyclic compound formed is benzothiofuran.

30. A cyclization process utilizing the catalyst copper aluminum borate which comprises the step of contacting (1) a starting compound having the general formula below:

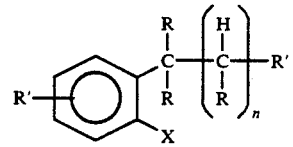

wherein X is —$NH_2$, —OH or SH; wherein the R' groups, being the same or different, are H or $C_1$ to $C_4$ hydrocarbyl; and the R groups, being the same or different, are H or substantially hydrocarbyl, and n=1 or 2; with (2) a catalyst consisting essentially of at least one member selected from the group consisting of (a) crystalline copper aluminum borate having the significant x-ray diffraction lines set forth in Table A and (b) zero valent copper on a support comprising at least one member selected from the group consisting of $Al_4B_2O_9$ and said crystalline copper aluminum borate, the zero valent copper on the support being formed by the reduction of the crystalline copper aluminum borate, said cyclization process being conducted under conditions sufficient to effect ring closure resulting in the formation of a heterocyclic fused ring compound.

31. The cyclization process of claim 30 wherein n=2.

32. The cyclization process of claim 30 wherein n=1.

* * * * *

UNITED STATES PATENT AND TRADEMARK OFFICE
CERTIFICATE OF CORRECTION

PATENT NO. : 5,332,838
DATED : July 26, 1994
INVENTOR(S) : Patrick E. McMahon; Larry C. Satek It is certified that error appears in the above-indentified patent and that said Letters Patent is hereby corrected as shown below:

| Col. | Line | |
|---|---|---|
| 1 | 35 | "as strychnine and resetpine." should read --as strychnine and reserpine.-- |
| 4 | 19 | "from 0 to 16" should read --from 0 to 1.6-- |
| 4 | 20 | "from 0 to 8" should read --from 0 to 0.8-- |
| 4 | 24 | "no more than 50°C.," should read --no more than 350°C.,-- |
| 8 | 48 | "from about 6500 to about 10000" should read --from about 650° to about 1000°-- |
| 13 | 5 | "300°C. a rate of 90°C." should read --300°C at a rate of 90°C.-- |
| 13 | 61 | "$Ni(NO_3)2 \cdot 2\ 1/2\ H_2O$" should read --$Ni(NO_3)_2 \cdot H_2O$--. |
| 14 | 27 | "$15m^2/g$" should read --$15m_2/g$-- |

UNITED STATES PATENT AND TRADEMARK OFFICE
CERTIFICATE OF CORRECTION

PATENT NO.  : 5,332,838
DATED       : July 26, 1994
INVENTOR(S) : Patrick E. McMahon; Larry C. Satek It is certified that error appears in the above-indentified patent and that said Letters Patent is hereby corrected as shown below:

| Col. | Line | |
|------|------|---|
| 14 | 62 | "Separately, 1.588g of PHF" should read --Separately, 1,588g of PHF-- |
| 16 | 8 | "arm, 50°C. initial temperature" should read --atm, 50°C. initial temperature-- |
| 19 | 28 | "ratio 13/1 to 1, catalyst" should read --ratio 13/1 to 19/1, catalyst-- |
| 20 | 30 | "oxygen, of sulfur atom" should read --oxygen, or sulfur atom-- |
| 21 | 24 | "(a) crystalline copper on a support" should read --(a) crystalline copper aluminum borate having the significant x-ray diffraction lines set forth in Table A and (b) zero valent copper on a support-- |

Signed and Sealed this

Thirtieth Day of April, 1996

Attest:

BRUCE LEHMAN

*Attesting Officer*          *Commissioner of Patents and Trademarks*